United States Patent
Akkerman et al.

(10) Patent No.: US 9,415,147 B2
(45) Date of Patent: *Aug. 16, 2016

(54) HIGH EFFICIENCY BLOOD PUMP

(71) Applicant: EVERHEART SYSTEMS INC., Webster, TX (US)

(72) Inventors: Neil H. Akkerman, Houston, TX (US); Greg S. Aber, Houston, TX (US)

(73) Assignee: EverHeart Systems Inc., Webster, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/973,593

(22) Filed: Dec. 17, 2015

(65) Prior Publication Data

US 2016/0101224 A1   Apr. 14, 2016

Related U.S. Application Data

(63) Continuation of application No. 12/899,748, filed on Oct. 7, 2010, now Pat. No. 9,227,001.

(51) Int. Cl.
*A61M 1/10* (2006.01)
*A61M 1/12* (2006.01)

(52) U.S. Cl.
CPC ............ *A61M 1/1017* (2014.02); *A61M 1/101* (2013.01); *A61M 1/1015* (2014.02); *A61M 1/1036* (2014.02); *A61M 1/122* (2014.02); *A61M 2205/8206* (2013.01)

(58) Field of Classification Search
CPC ..... A61M 1/10; A61M 1/101; A61M 1/1012; A61M 1/1013; A61M 1/1015; A61M 1/1017; A61M 1/1029; A61M 1/1036
See application file for complete search history.

(56) References Cited

U.S. PATENT DOCUMENTS

| | | | |
|---|---|---|---|
| 4,643,641 A | 2/1987 | Clausen et al. |
| 4,984,972 A | 1/1991 | Clausen et al. |
| 5,017,103 A | 5/1991 | Dahl |
| 5,049,134 A | 9/1991 | Golding et al. |
| 5,290,227 A | 3/1994 | Pasque |

(Continued)

FOREIGN PATENT DOCUMENTS

| | | |
|---|---|---|
| EP | 1113177 A2 | 7/2001 |
| WO | WO-92/21388 A1 | 12/1992 |

(Continued)

OTHER PUBLICATIONS

Lawrence Pumps. "Run Times", vol. 2, Issue No. 1, Jan. 2005.

(Continued)

*Primary Examiner* — Eugene Wu
(74) *Attorney, Agent, or Firm* — Nathan S. Smith; McDermott Will & Emery LLP (57) ABSTRACT

A high efficiency blood pump includes a pump housing, wherein the pump housing provides an inlet and outlet. The pump includes a motor housing, wherein the motor housing contains a motor. An impeller is housed in the pump housing, wherein the impeller is radially supported by a hydrodynamic bearing providing at least one row of pattern grooves. A diaphragm provided by the pump housing separates the impeller chamber from the motor chamber. A magnetic coupling is provided between the motor and the impeller, wherein the magnetic coupling causes the impeller to rotate when the motor rotates and provides axial restraint of the impeller.

18 Claims, 13 Drawing Sheets

(56) References Cited

U.S. PATENT DOCUMENTS

| | | | |
|---|---|---|---|
| 5,370,509 A * | 12/1994 | Golding | A61M 1/101 415/900 |
| 5,611,679 A | 3/1997 | Ghosh et al. | |
| 5,890,883 A | 4/1999 | Golding et al. | |
| 5,947,703 A * | 9/1999 | Nojiri | A61M 1/101 415/229 |
| 6,015,272 A * | 1/2000 | Antaki | A61M 1/101 415/900 |
| 6,048,363 A | 4/2000 | Nagyszalanczy et al. | |
| 6,071,093 A * | 6/2000 | Hart | A61M 1/101 384/100 |
| 6,158,984 A | 12/2000 | Cao et al. | |
| 6,181,040 B1 | 1/2001 | Schob | |
| 6,227,797 B1 | 5/2001 | Watterson et al. | |
| 6,234,772 B1 | 5/2001 | Wampler et al. | |
| 6,302,910 B1 | 10/2001 | Yamazaki et al. | |
| 6,445,956 B1 | 9/2002 | Laird et al. | |
| 6,547,530 B2 | 4/2003 | Ozaki et al. | |
| 6,589,031 B2 | 7/2003 | Maeda et al. | |
| 6,808,371 B2 | 10/2004 | Niwatsukino et al. | |
| 6,894,456 B2 | 5/2005 | Tsukamoto et al. | |
| 7,616,997 B2 | 11/2009 | Kieval et al. | |
| 7,682,301 B2 | 3/2010 | Wampler et al. | |
| 7,699,586 B2 | 4/2010 | LaRose et al. | |
| 8,114,008 B2 | 2/2012 | Hidaka et al. | |
| 8,551,163 B2 | 10/2013 | Aber et al. | |
| 8,901,775 B2 | 12/2014 | Armstrong et al. | |
| 9,227,001 B2 | 1/2016 | Akkerman et al. | |
| 2003/0091249 A1 | 5/2003 | Kurimura et al. | |
| 2003/0124007 A1 * | 7/2003 | Schima | A61M 1/1017 417/420 |
| 2003/0175119 A1 | 9/2003 | Tajima et al. | |
| 2004/0236420 A1 | 11/2004 | Yamane et al. | |
| 2005/0025630 A1 | 2/2005 | Ayre et al. | |
| 2005/0095151 A1 | 5/2005 | Wampler et al. | |
| 2005/0281685 A1 | 12/2005 | Woodard et al. | |
| 2005/0287022 A1 | 12/2005 | Yaegashi et al. | |
| 2006/0155159 A1 | 7/2006 | Melvin | |
| 2006/0245955 A1 | 11/2006 | Horiuchi et al. | |
| 2008/0124231 A1 | 5/2008 | Yaegashi | |
| 2008/0269880 A1 | 10/2008 | Jarvik | |
| 2009/0112626 A1 | 4/2009 | Talbot et al. | |
| 2009/0234447 A1 | 9/2009 | LaRose et al. | |
| 2009/0270679 A1 | 10/2009 | Hoeg et al. | |
| 2010/0045114 A1 | 2/2010 | Sample et al. | |
| 2010/0063347 A1 | 3/2010 | Yomtov et al. | |
| 2010/0164296 A1 | 7/2010 | Kurs et al. | |
| 2010/0185280 A1 | 7/2010 | Ayre et al. | |
| 2011/0188996 A1 | 8/2011 | Hoshi et al. | |
| 2011/0238172 A1 | 9/2011 | Akdis | |
| 2012/0089225 A1 | 4/2012 | Akkerman et al. | |
| 2012/0280305 A1 | 11/2012 | Zhu et al. | |
| 2013/0241306 A1 | 9/2013 | Aber et al. | |
| 2013/0345493 A1 | 12/2013 | Aber et al. | |
| 2014/0200664 A1 | 7/2014 | Akkerman et al. | |
| 2014/0255225 A1 | 9/2014 | Aber et al. | |
| 2015/0061591 A1 | 3/2015 | Armstrong et al. | |

FOREIGN PATENT DOCUMENTS

| WO | WO-2009/091267 A2 | 7/2009 |
|---|---|---|
| WO | WO-2009/104451 A1 | 8/2009 |

OTHER PUBLICATIONS

Zirkelback, et al., "Finite Element Analysis of Herringbone Groove Journal Bearings: A Parametric Study," Transactions of the ASME, Apr. 1998, pp. 234-240, vol. 120.

El-Moli, "Study of Parameters Influencing Design Factors of Oil-Lubricated Herringbone Grooved Journal Bearing," Post Graduate Thesis, Jan. 25, 2004.

John Crane, "Multilobe Bearings," Nov. 2008, 48 pages.

* cited by examiner

FIG. 1

FIG. 2
(SECTION A - A)

FIG. 3
(SECTION B - B)

FIG 4
(DETAIL C)

FIG. 13
(DETAIL D)

CONVEX

FIG. 16B

CONCAVE

FIG. 16C

CONVEX

FIG. 16D

CONCAVE

FIG. 16E

FIG. 17
(DETAIL E)

(Section G-G)

FIG.20
(DETAIL H)

HIGH EFFICIENCY BLOOD PUMP

RELATED APPLICATION

This application is a continuation of U.S. patent application Ser. No. 12/899,748, filed Oct. 7, 2010, and issued as U.S. Pat. No. 9,227,001, the entirety of which is hereby incorporated by reference herein.

FIELD OF THE INVENTION

This invention relates to implantable rotary blood pumps.

BACKGROUND OF INVENTION

Some blood pumps mimic the pulsatile flow of the heart and have progressed to designs that are non-pulsatile. Non-pulsatile or continuous flow pumps are typically rotary and propel fluid with impellers that span the spectrum from radial flow centrifugal type impellers to axial flow auger type impellers.

A common issue encountered by blood pumps is blood damage. The causes of blood damage are mostly attributed to shear stress and heat generated by the bearings supporting the impeller and/or shaft seals of externally driven impellers. Shear stress and/or heat may cause hemolysis, thrombosis, and the like.

A great deal of effort has been devoted to reducing or eliminating blood damage in rotary blood pumps. One solution to minimizing/eliminating blood damage is to provide total hydrodynamic support of the impeller. For example, ramp, wedge, plain journal, or groove hydrodynamic bearings may be utilized to provide hydrodynamic support in blood pumps.

Additionally, passive permanent magnetic and active controlled magnetic bearings can be utilized to provide impeller support in blood pumps. Magnetic bearings may be combined with hydrodynamic bearings to provide total impeller support in blood pumps.

Some blood pumps provide blood flow utilizing a motor that has a shaft mechanically connected to an impeller. Shaft seals may be utilized to separate the motor chamber from the pump chamber. However, shaft seals can fail and generate excess heat allowing blood to enter the motor and/or produce blood clots. Some blood pumps incorporate electric motors into the pumping chamber, rather than providing separate motor and pumping chambers. For example, a stator may be provided in the pump housing and magnets can be incorporated into an impeller to provide a pump impeller that also functions as the rotor of the electric motor.

Heart pumps that are suitable for adults may call for approximately 5 liters/min of blood flow at 100 mm of Hg pressure, which equates to about 1 watt of hydraulic power. Some implantable continuous flow blood pumps consume significantly more electric power to produce the desired amount of flow and pressure.

High power consumption makes it impractical to implant a power source in the body. For example, size restrictions of implantable power sources may only allow the implantable power source to provide a few hours of operation. Instead, high power consumption blood pumps may provide a wire connected to the pump that exits the body (i.e. percutaneous) for connection to a power supply that is significantly larger than an implantable power source. These blood pumps may require external power to be provided at all times to operate. In order to provide some mobility, external bulky batteries may be utilized. However, percutaneous wires and external batteries can still restrict the mobility of a person with such a blood pump implant. For example, such high power consumption blood pumps have batteries that frequently require recharging thereby limiting the amount of time the person can be away from a charger or power source, batteries that can be heavy or burdensome thereby restricting mobility, percutaneous wires that are not suitable for prolonged exposure to water submersion (i.e. swimming, bathing, etc.), and/or other additional drawbacks.

The various embodiments of blood pumps discussed herein may be suitable for use as a ventricular assist device (VAD) or the like because they cause minimal blood damage, are energy efficient, and can be powered by implanted batteries for extended periods of time. Further, these pumps are also beneficial because they may improve the quality of life of a patient with a VAD by reducing restrictions on the patient's lifestyle.

SUMMARY OF THE INVENTION

The discussion herein provides a description of a high efficiency blood pump that is energy efficient, causes minimal blood damage, and improves quality of life.

An embodiment of a blood pump includes a pump housing, wherein the pump housing provides an inlet and outlet. The blood pump also includes an impeller housed in the pump housing, wherein the impeller is radially supported by a first hydrodynamic bearing that provides at least one row of flow inducing pattern grooves.

Another embodiment of a blood pump includes a pump housing, wherein the pump housing provides an inlet and outlet. The blood pump also includes an impeller housed in the pump housing, wherein the impeller is axially supported by a first hydrodynamic bearing that provides at least one row of flow inducing pattern grooves.

Yet another embodiment of a pump includes a pump housing providing an inlet and outlet and a motor housing, wherein the motor housing houses a motor. The pump also includes an impeller housed in the pump housing that is radially supported by a hydrodynamic bearing that provides at least one row of pattern grooves. The pump also provides a magnetic coupling between the motor and the impeller, wherein the magnetic coupling causes the impeller to rotate when the motor rotates.

DETAILED DESCRIPTION

Refer now to the drawings wherein depicted elements are not necessarily shown to scale and wherein like or similar elements are designated by the same reference numeral through the several views.

The following detailed description provides an implantable, energy efficient, small, sealess, and magnetically driven blood pump. The blood pump is capable of operating for extended periods of time on a single charge. For example, the energy efficient blood pump may be suitable for use with an implanted rechargeable power source or the like. The pump can be installed pericardially (i.e. near the heart) with less complex surgical procedures. Those skilled in the art will appreciate that the various features discussed below can be combined in various manners, in addition to the embodiments discussed below. The scope of the claims is in no way limited to the specific embodiments discussed herein.

Figure 1:
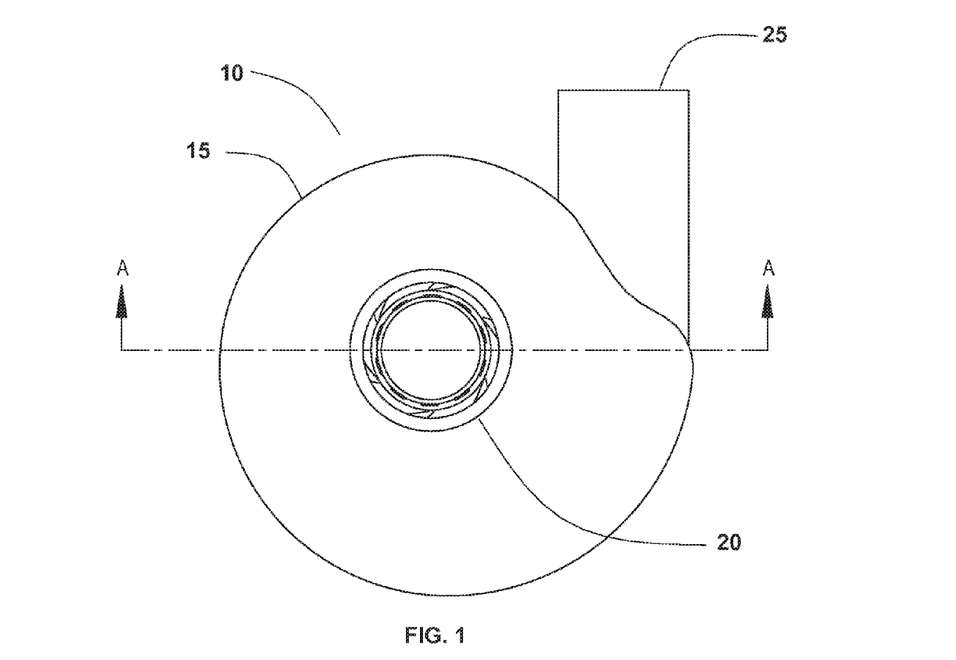
FIG. 1 is a top view of an illustrative embodiment of a pump.

FIG. 1 is a top view of an illustrative embodiment of pump 10. Pump 10 is formed from pump housing 15 providing inlet 20 and outlet 25 and motor housing 35. Pump housing 15 is composed of two or more pieces and may be joined by welding. However, in other embodiments, pump housing 15 may be joined by fusing, press fit, threading, screw and elastomeric sealing, bonding, fasteners, and/or any other suitable joining method or combinations of joining methods. Motor housing 35 may be joined to pump housing 15 by welding, fusing, press fit, threading, screw and elastomeric sealing, bonding, fasteners, and/or any other suitable joining method or combinations of joining methods. Line A-A passing through pump housing 15 indicates the plane from which the cross-sectional view in FIG. 2 is provided.

Figure 2:
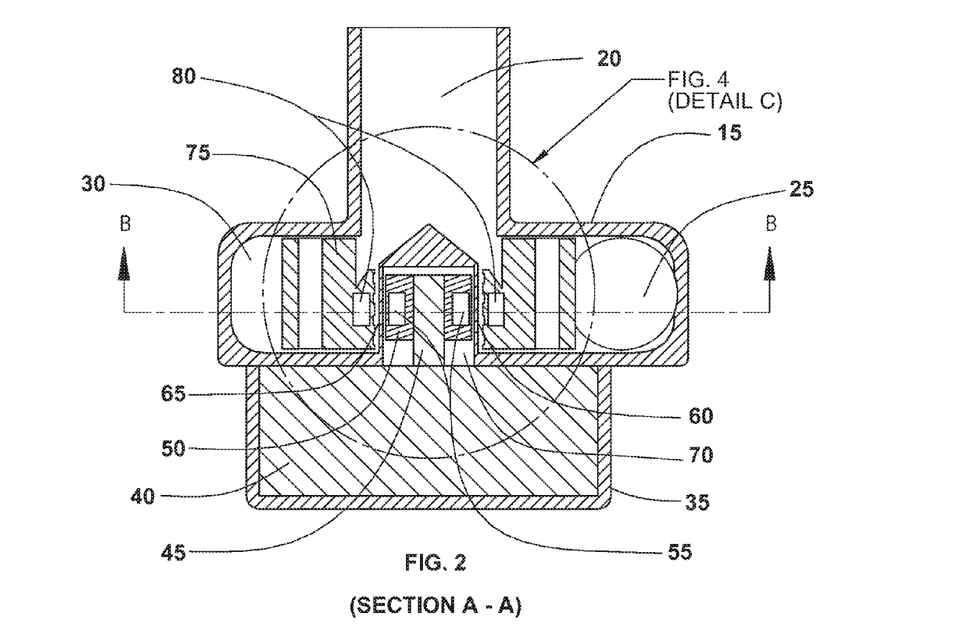
FIG. 2 is a cross-sectional side view of an illustrative embodiment of a pump.

FIG. 2 is a cross-sectional side view of an illustrative embodiment of pump 10. Pump housing 15 provides impeller chamber 30 for impeller 75. Impeller chamber 30 has inlet 20 for connection to a fluid source and outlet 25 for providing fluid to a desired location. Impeller chamber 30 is sealed and pressure tight to prevent fluid from entering/exiting impeller chamber 30 from locations other than inlet 20 and outlet 25.

Figure 7:
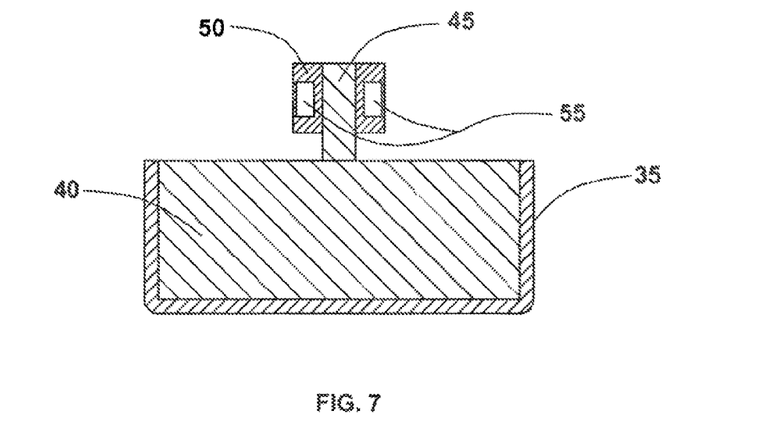
FIG. 7 is a cross-sectional view of an illustrative embodiment of a motor housing of a pump.

Motor housing 35 is attached to pump housing 15 to form a fluid and/or pressure tight chamber for motor 40. While motor housing 35 is shown as a separate component from pump housing 15, in other embodiments, pump housing 15 and motor housing 35 may be combined to form a single combined housing. A cross-sectional view of an illustrative embodiment of motor 40 and motor housing 35 of pump 10 is shown in FIG. 7. In particular, motor housing 35 is shown separate from pump 10. Motor 40 is entirely contained between pump housing 15 and motor housing 35. A high efficiency electric motor can be utilized, such as an electric motor with efficiency of about 85% or greater. However, in other embodiments, any other suitable driving means can be utilized. Motor 40 provides shaft 45 with hub 50 mounted to shaft 45. Hub 50 contains one or more permanent magnets and/or magnetic materials 55. Motor 40 rotates shaft 50 causing permanent magnets 55 placed in hub 50 to rotate. In some embodiments, a motor with a useful life of greater than 10 years is utilized. Further, the motor may utilize hydrodynamic bearings with fluid support provided by a fluid other than blood.

Figure 6:
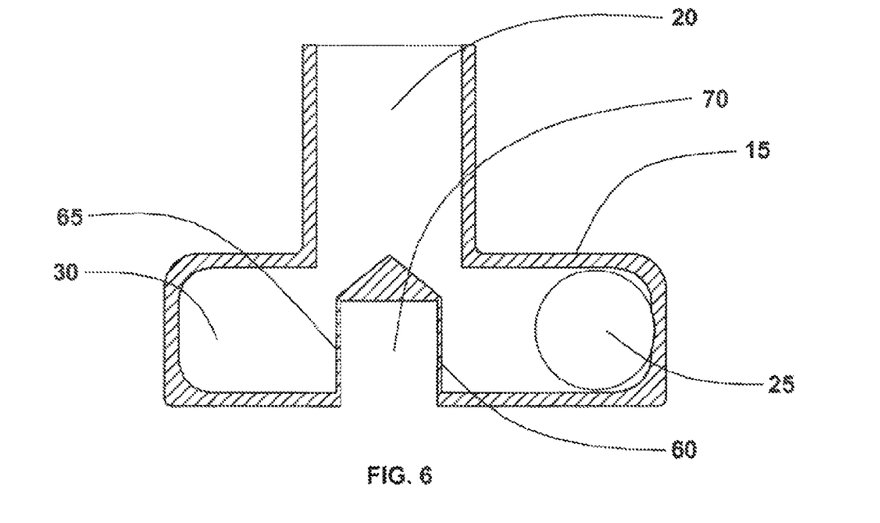
FIG. 6 is a cross-sectional view of an illustrative embodiment of a pump housing.

A cross-sectional view of an illustrative embodiment of pump housing 15 without impeller 75 is shown in FIG. 6. Pump housing 15 may provide a non-ferromagnetic and/or non-electrically conductive diaphragm 60 separating impeller chamber 30 from the chamber housing motor 40. Diaphragm 60 defines cavity 70 providing a region for hub 50 to rotate within. Additionally, diaphragm 60 may provide cylindrical bearing surface 65 for impeller 75 to rotate around with hydrodynamic radial support. Impeller 75 includes one or more permanent magnets and/or magnetic materials 80. Permanent magnets 80 allow impeller 75 to be magnetically coupled to hub 50. This magnetic coupling allows motor 40 to cause impeller 75 to rotate when motor 40 rotates hub 50.

Figure 3:
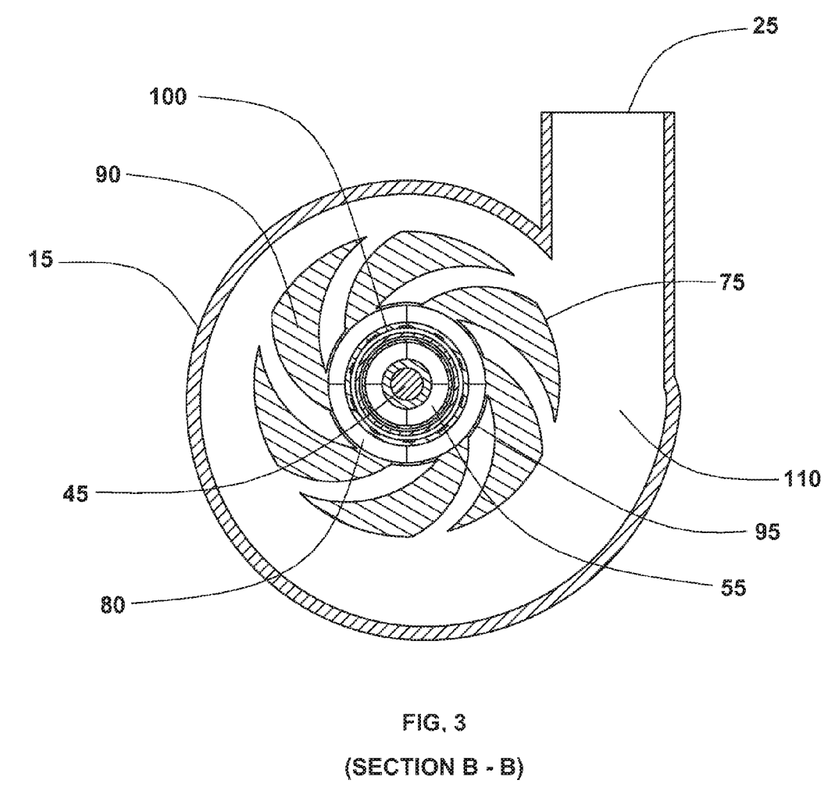
FIG. 3 is a cross-sectional top view of an illustrative embodiment of a pump.

Line B-B passing through pump housing 15 indicates the plane from which the cross-section view in FIG. 3 is provided. FIG. 3 is a cross-sectional top view of an illustrative embodiment of pump 10. Impeller 75 is composed of an array of arc shaped segments 90 joined by central ring 95. Pump housing 15 has volute 110 feeding the outlet 25. In other embodiments, volute 110 could be omitted from pump housing 15 and outlet 25 could have any suitable orientation and shape. Pump housing 15 is designed in a manner where impeller 75, when rotated, pressures and moves fluid received from inlet 20 to outlet 25.

Permanent magnets 55 in hub 50 and permanent magnets 80 in central ring 95 of impeller 75 form a magnetic coupling between the impeller 75 and hub 50. In contrast to radial magnetic bearings that are arranged to repel each other, permanent magnets 55 and 80 are arranged so that they are attracted to each other. In order to minimize radial loads, permanent magnets 55 and 80 provide a minimal magnetic coupling or just enough of a magnetic coupling to rotate impeller 75 under load. The attractive force of the magnetic coupling of permanent magnets 55 and 80 also provides axial restraint of impeller 75. For example, axial movement of impeller 75 would misalign permanent magnets 55 and 80. The magnetic forces of permanent magnets 55 and 80 would restrain and re-align the magnets. Because of the magnetic forces caused by permanent magnets 55 and 80, axial movement of impeller 75 may cause axial force to be exerted on shaft 45 and hub 50 of motor 40, which is then transferred to bearing(s) (not shown) of motor 40.

Permanent magnets 80 may be sufficiently small in size that they have no impact on the main fluid flow paths of impeller 75, thereby allowing the design of impeller 75 to focus on fully optimizing pump efficiency. These benefits can allow pumping efficiencies of greater than 50% to be achieved.

Figure 5:
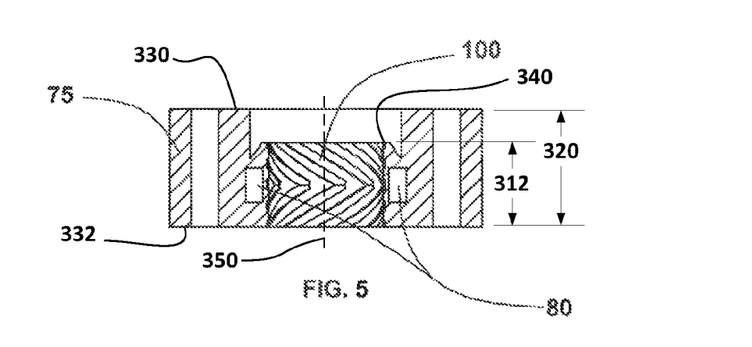
FIG. 5 is a cross-sectional view of an illustrative embodiment of an impeller.
Figure 8:
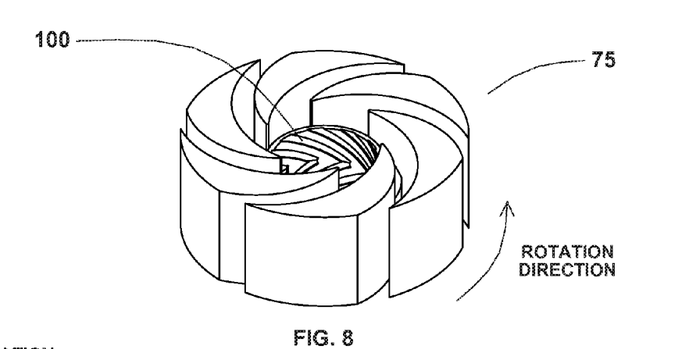
FIG. 8 is an isometric view of an illustrative embodiment of an impeller.

Impeller internal surface 100 of central ring 95 is utilized to form a hydrodynamic bearing between cylindrical bearing surface 65 and impeller internal surface 100. Impeller 75 is configured to rotate within impeller chamber 30 with full radial hydrodynamic support from the hydrodynamic bearing formed by cylindrical bearing surface 65 and impeller internal surface 100. A cross section view of an illustrative embodiment of impeller 75 is shown in FIG. 5 and an isometric view of an illustrative embodiment of impeller 75 is shown in FIG. 8, which more thoroughly illustrate the hydrodynamic bearing.

Pattern grooves on impeller internal surface 100 of impeller 75 create a high pressure zone when impeller 75 is rotated, thereby creating a hydrodynamic bearing. For example, symmetrical herringbone grooves create a high pressure zone where the two straight lines of the V-shape grooves meet or the central portion of the symmetrical herringbone grooves. The pressure created by the pattern grooves on impeller internal surface 100 acts as a radial stabilizing force for impeller 75 when it is rotating concentrically. While the embodiment shown provides symmetrical herringbone grooves on internal surface 100 of impeller 75, a variety of different groove patterns may be utilized on impeller internal surface 100 to provide a hydrodynamic bearing, which is discussed in detail below. Because low loads are exerted on impeller 75, the radial hydrodynamic bearing formed between cylindrical bearing surface 65 and impeller internal surface 100 can provide stable radial support of impeller 75.

Impeller 75 may be an open, pressure balanced type impeller to minimize axial thrust. Impeller 75 is considered to be open because there is no endplate on either side of arc shaped segments 90. Further, impeller 75 is considered to be pressure balanced because it is designed to minimize axial thrust during the rotation of impeller 75. However, other types of impellers may be suitable in other embodiments. Impeller 75 could be any other suitable blade shape, rotate in the opposite direction, or non-pressure balanced. For example, other suitable impellers may be semi-open type (i.e. end plate on one side of impeller) or closed type (i.e. end plate on both sides of impeller).

Figure 4:
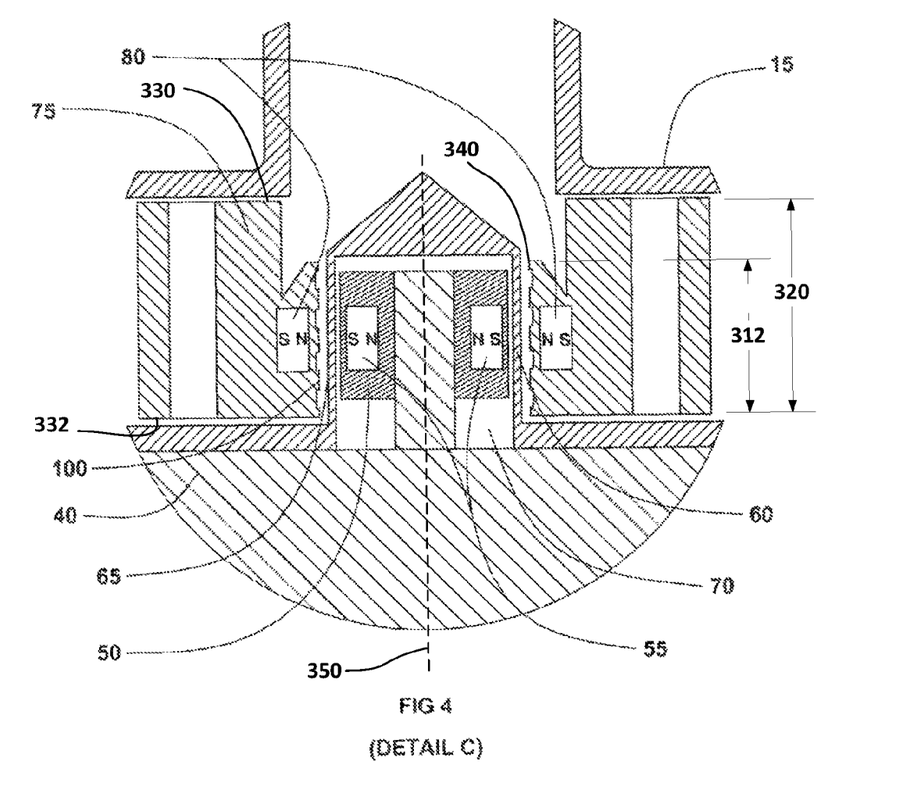
FIG. 4 is a close up cross-sectional view of an area of an illustrative embodiment of a pump.

FIG. 4 is a close up cross-sectional view of an area C (see FIG. 2) of an illustrative embodiment of pump 10. The magnetic coupling transmits torque from shaft 45 of the motor 40 to impeller 75. In the embodiment shown, permanent magnets 55 and 80 are radially distributed around hub 50 and impeller 75. The poles of permanent magnets 55 and 80 are arranged to attract to each other. The attractive force of the magnetic coupling of permanent magnets 55 and 80 provides axial restraint of impeller 75. While permanent magnets 55 and 80 are shown as arc shaped like quadrants of a cylinder, it should be recognized that permanent magnets 55 and 80 may be shaped in a variety of different manners to provide the magnetic coupling. For example, one or more ring shaped magnets polarized with arc shaped magnetic regions, square/rectangular shaped, rod shaped, disc shaped, or the like may be utilized. In the magnetic coupling arrangement shown, permanent magnets 80 are shown in the internal portion of impeller 75. Internal magnetic couplings, similar to the arrangement shown, can be more efficient than face or external type magnetic couplings that place the magnets in the blades of an impeller or rotor because they have a smaller diameter and less eddy current losses. Diaphragm 60, intermediate the coupling, is non-ferromagnetic and/or non-electrically conductive to minimize eddy current losses. For example, couplings with non-electrically conducting diaphragms such as bio-compatible ceramic, glass or the like, would exhibit less eddy current losses than those with electrically conducting diaphragms.

In one embodiment, motor 40 is of the brushless DC, sensorless, iron core type electric motor with fluid dynamic bearings. However, in other embodiments, any suitable type of motor including one or more features such as, but not limited to, brushed, hall-effect sensored, coreless, and Halbach array or any type of bearing such as ball or bushing may be used. Motor housing 35 may include motor control circuitry or be configured to operate with remotely located control circuits.

Separating motor 40 from impeller chamber 30 may allow a high efficiency motor to be utilized. For example, incorporating components into a pump impeller to form the rotor of an electric motor may compromise the design of the pump impeller resulting in reduced efficiency. Further, designing a rotor and stator that is incorporated into the design of a pump may result in an electric motor with large gaps between components of the rotor and stator, thereby decreasing the efficiency of the motor. The magnetic coupling arrangements utilized in the embodiments discussed herein allow a highly efficient motor design to be utilized without compromising the design of an efficient pump impeller.

Figure 12A:
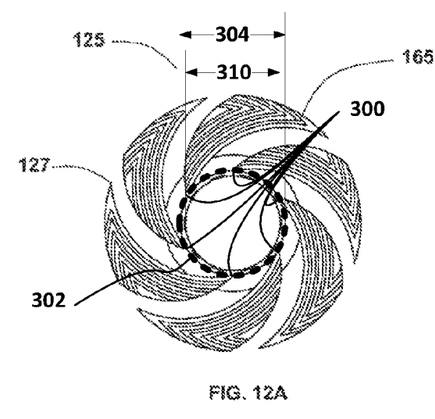
FIGS. 12A and 12B are top views of illustrative embodiments of impellers with spiral herringbone grooves and spiral grooves.
Figure 12B:
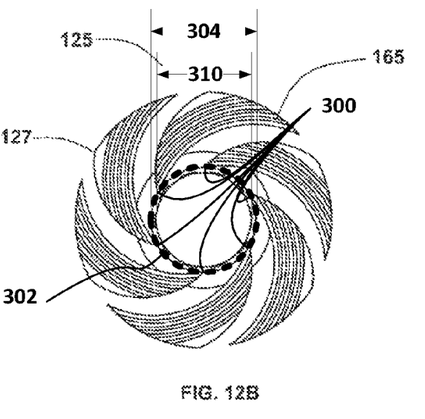

As shown in FIGS. 4-5, a maximum height 320 of the plurality of blades 90 overlaps with the internal surface 100, having a height 312, the maximum height 320 being in a direction of an axis 350 of impeller rotation. As shown in FIG. 4, a topmost extent 330 of the plurality of blades 90 is axially closer to the inlet 20 than is (a) a topmost extent 340 of the hydrodynamic bearing and (b) a bottom 332 of the plurality of blades 90. As shown in FIGS. 12A and 12B, a maximum cross-sectional dimension 304 of a shape 302 inscribed by all radially innermost edges 300 of the plurality of blades 90 is greater than a maximum cross-sectional dimension 310 of the impeller internal surface 100.

Figure 9A:
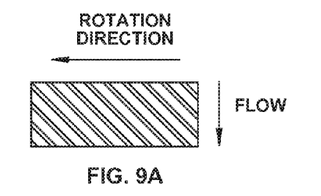
FIG. 9A-9K are illustrative embodiments of various types of pattern grooves.
Figure 9B:
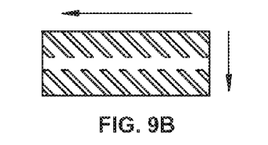
Figure 9C:
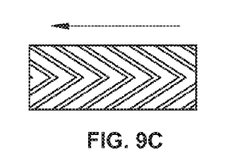
Figure 9D:
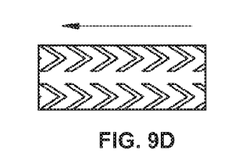
Figure 9E:
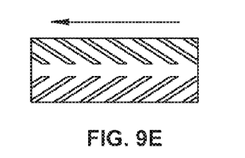
Figure 9F:
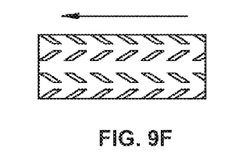
Figure 9G:
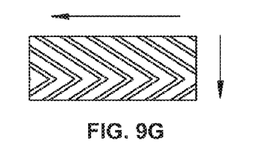
Figure 9H:
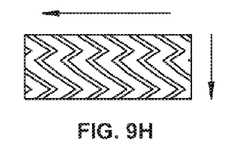
Figure 9I:
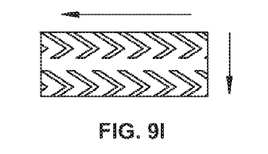
Figure 9J:
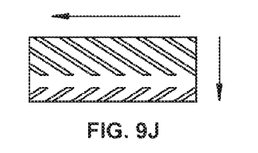
Figure 9K:
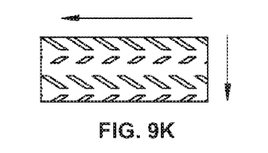
Figure 10A:
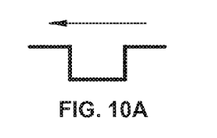
FIG. 10A-10D are cross-sectional views of various shapes of pattern grooves.
Figure 10B:
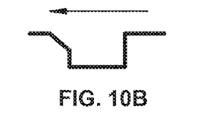
Figure 10C:
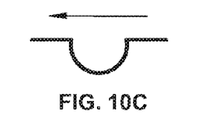
Figure 10D:
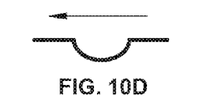

FIGS. 9A-9K and 10A-10D illustrate various embodiments of pattern grooves that may be implemented on impeller internal surface 100. As discussed previously, impeller internal surface 100 provides a hydrodynamic journal bearing. For example, impeller internal surface 100 may utilize patterned grooves. The pattern grooves may be of any type including, but not limited to, half herringbone (FIG. 9A), dual half herringbone (FIG. 9B), symmetrical herringbone (FIG. 9C), dual symmetrical herringbone (FIG. 9D), open symmetrical herringbone (FIG. 9E), open dual symmetrical herringbone (FIG. 9F), asymmetrical herringbone (FIG. 9G), continuous asymmetrical dual herringbone (FIG. 9H), asymmetrical dual herringbone (FIG. 9I), asymmetrical open herringbone (FIG. 9J), asymmetrical open dual herringbone (FIG. 9K), or the like. Flow inducing pattern grooves, such as half herringbone patterns and asymmetrical herringbone patterns, have the added benefit of producing a substantial secondary flow, particularly along the axis of impeller rotation between cylindrical bearing surface 65 and impeller 75, thereby minimizing stagnant flow between cylindrical bearing surface 65 and impeller 75. Because stagnant areas may cause blood clots to form in blood pumps, the secondary flow reduces the chances of blood clots forming. Further, asymmetrical herringbone patterns have the additional benefit over half herringbone patterns in that they provide similar radial stiffness as symmetrical herringbone patterns. As shown in FIG. 10A-10D, each of the pattern grooves of internal surface 100 can be shaped in a variety of different manners, such as, but not limited to, rectangular grooves, rectangular grooves with a bevel, semi-circular grooves, elliptical grooves, or the like. In other embodiments, impeller internal surface 100 may also be a plain journal bearing without pattern grooves or a multi-lobe shape that creates a hydrodynamic bearing. In alternative embodiments, the pattern grooves or multi-lobe shapes may be located on the surface of cylindrical bearing surface 65 facing impeller 75 rather than impeller internal surface 100 or the pattern grooves may be located on an outer radial surface of impeller 75 or internal radial surface of pump housing 15 facing the impeller 75.

Figure 11:
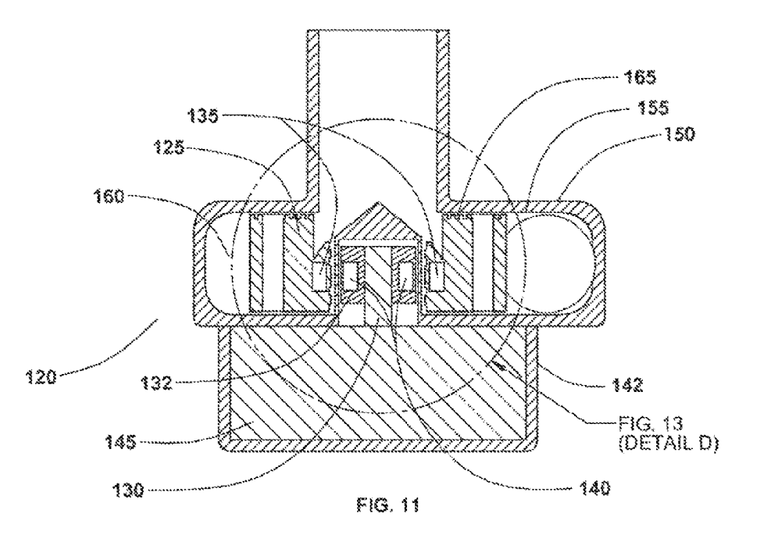
FIG. 11 is a cross-sectional side view of an illustrative embodiment of a pump with an axial hydrodynamic bearing.

FIG. 11 provides a cross-sectional side view of an illustrative embodiment of housing 150 for pump 120. Similar to the embodiment shown in FIG. 2, pump 120 provides pump housing 150, impeller 125, shaft 130, hub 132, permanent magnets 135 and 140, motor housing 142, motor 145, and impeller chamber 160, which all provide a similar function to the components discussed previously. These common elements may operate in substantially the same manner as previously described. The substantial differences in the embodiments are discussed below.

The embodiment shown in FIG. 2 provided radial support of impeller 75 utilizing a hydrodynamic bearing. However in FIG. 11, in addition to a radial hydrodynamic bearing, one or more external planar surfaces or top surfaces 165 of impeller 125 include pattern grooves providing partial axial hydrodynamic support.

Figure 13:
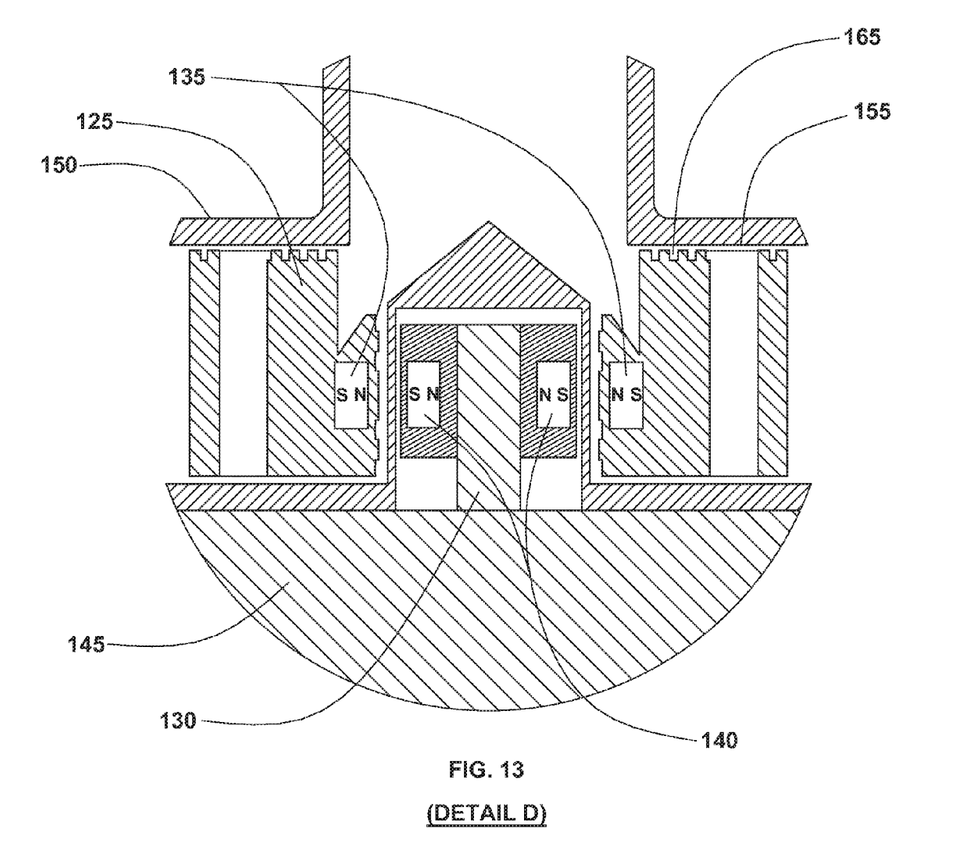
FIG. 13 is a close up cross-sectional view of an area of an illustrative embodiment of a pump with an axial hydrodynamic bearing.

FIG. 13 is a close up cross-sectional view of an area D of an illustrative embodiment of pump 120. Each arc shaped segment 127 of impeller 125 includes one or more pattern grooves on top surfaces 165. The pattern grooves on top surface 165 of impeller 125 and internal surface 155 of housing 150 form a hydrodynamic bearing providing partial axial hydrodynamic support that prevents or minimizes contact between impeller 125 and housing 150. The pattern grooves on top surface 165 are considered to be interrupted because they are separated by the flow channels of impeller 125.

Figure 14A:
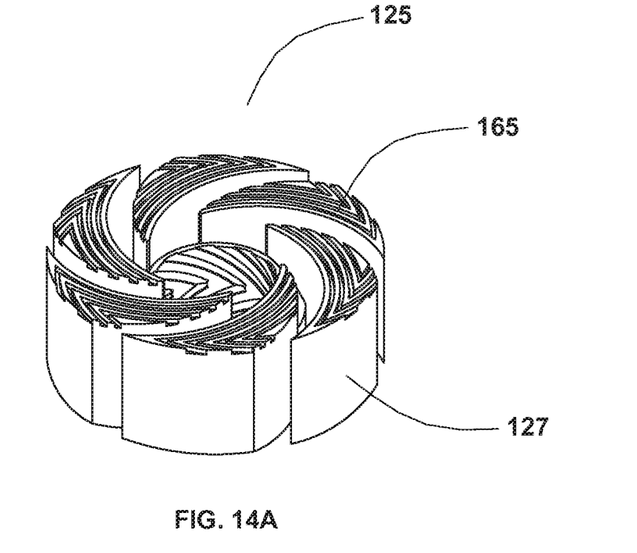
FIGS. 14A and 14B are isometric views of illustrative embodiment of impellers with spiral herringbone grooves and spiral grooves.
Figure 14B:
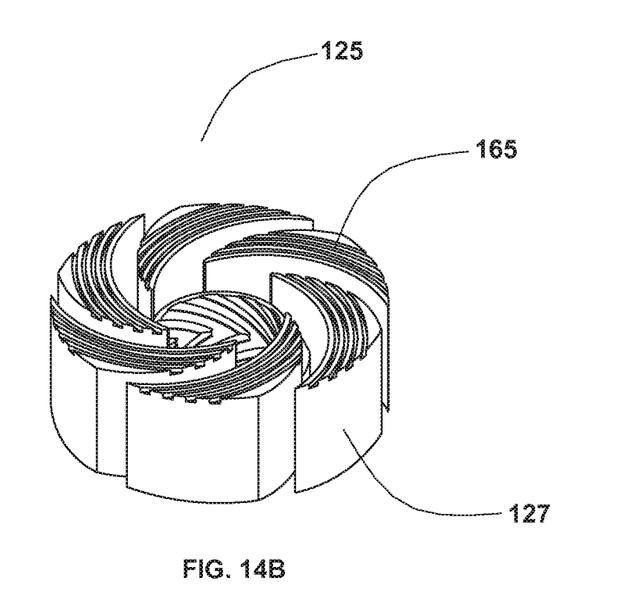

Pattern grooves on top surface of impeller 125 may be any suitable type of grooves including, but not limited to, spiral herringbone and spiral grooves shown in FIGS. 12A and 12B. FIGS. 14A and 14B respectively provide an isometric view of impeller 125 with spiral herringbone and spiral grooves. The arrangement of the pattern grooves on top surfaces 165 is balanced so that instability during rotation of impeller 125 is prevented or minimized. For example, all of the top surfaces 165 have pattern grooves in the embodiment shown. However, it should be recognized that in other embodiments a balanced arrangement of top surfaces 165 that have pattern grooves and do not have pattern grooves may be utilized. A balanced arrangement of top surfaces 165 prevents or minimizes the instability of impeller 125. Examples of balanced arrangements for the embodiment shown may include, but are not limited to, all top surfaces 165 with grooves or three alternating top surfaces 165 with grooves and three without grooves. Flow inducing pattern grooves, such as spiral and spiral herringbone grooves, have the added benefit of producing a substantial secondary flow, particularly between top surface 165 of impeller 75 and internal surface 155 of housing 150. Additionally, various pattern groove types including symmetrical, asymmetrical, open, and/or dual groove patterns and various groove shapes including rectangular, rectangular with a bevel, semi-circular, and elliptical shown in FIGS. 9A-9K and 10A-10D may be utilized. An additional benefit of the hydrodynamic bearing on top surface 165 of impeller 125 is that it increases impeller stability during rotation by restraining angular motion along axes normal to the axis of impeller rotation.

Figure 15:
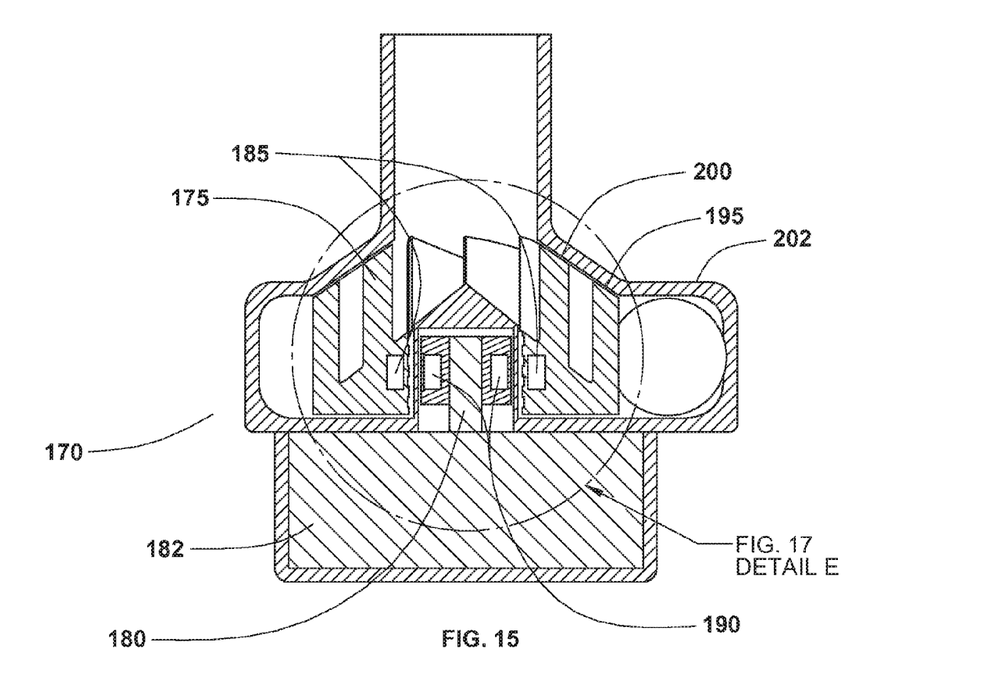
FIG. 15 is a cross-sectional side view of an illustrative embodiment of a pump with a conically shaped impeller.

FIG. 15 is a cross-sectional side view of an illustrative embodiment of pump 170 with a conically shaped impeller 175. Many of the components of pump 170 are substantially similar to the components of the previously discussed illustrative embodiments. These similar components may operate in substantially the same manner as previously described. As in the previously discussed embodiments, impeller 175 is magnetically coupled to shaft 180 of motor 182. Permanent magnets 185 and 190 couple motor 182 to impeller 175. However, in the embodiment shown, impeller 175 is formed in a generally conical shape. Top surfaces 195 of impeller 175 facing internal surface 200 of the pump housing 202 are shaped in a manner that provides a hydrodynamic bearing between impeller top surfaces 195 and internal surface 200.

Figure 16A:
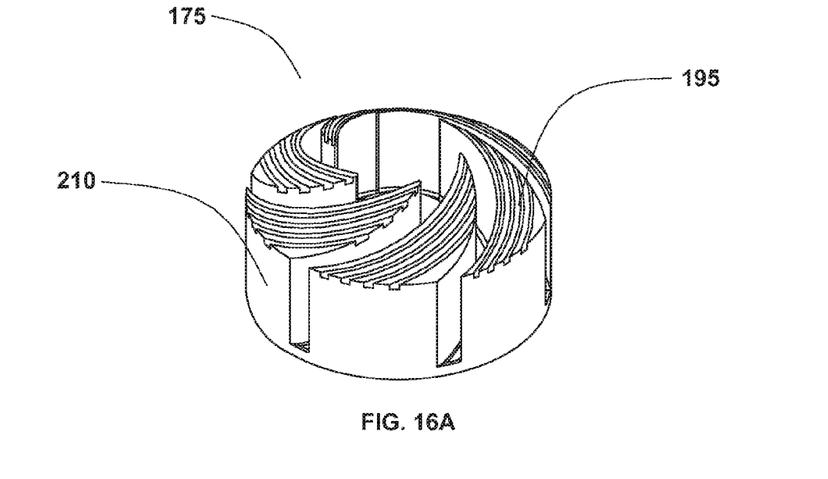
FIG. 16A-16E are isometric views of illustrative embodiments of conically shaped impellers.
Figure 16B:
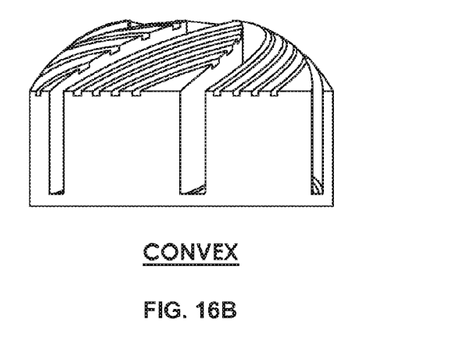
Figure 16C:
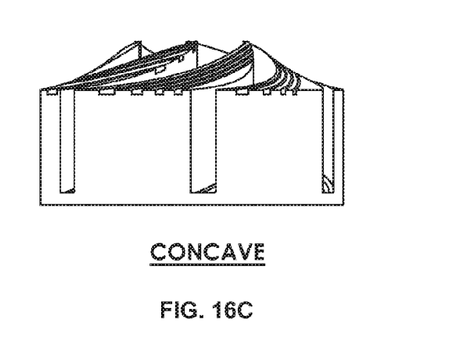
Figure 16D:
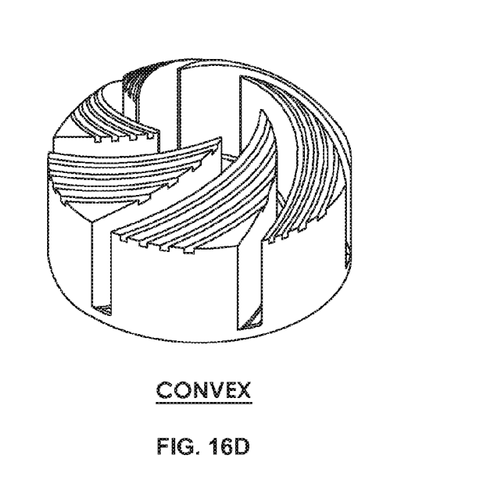
Figure 16E:
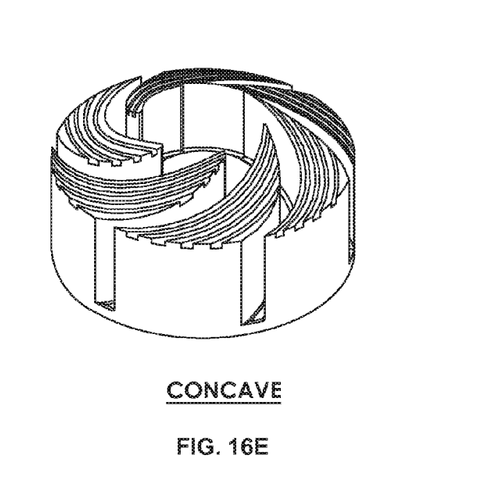
Figure 17:
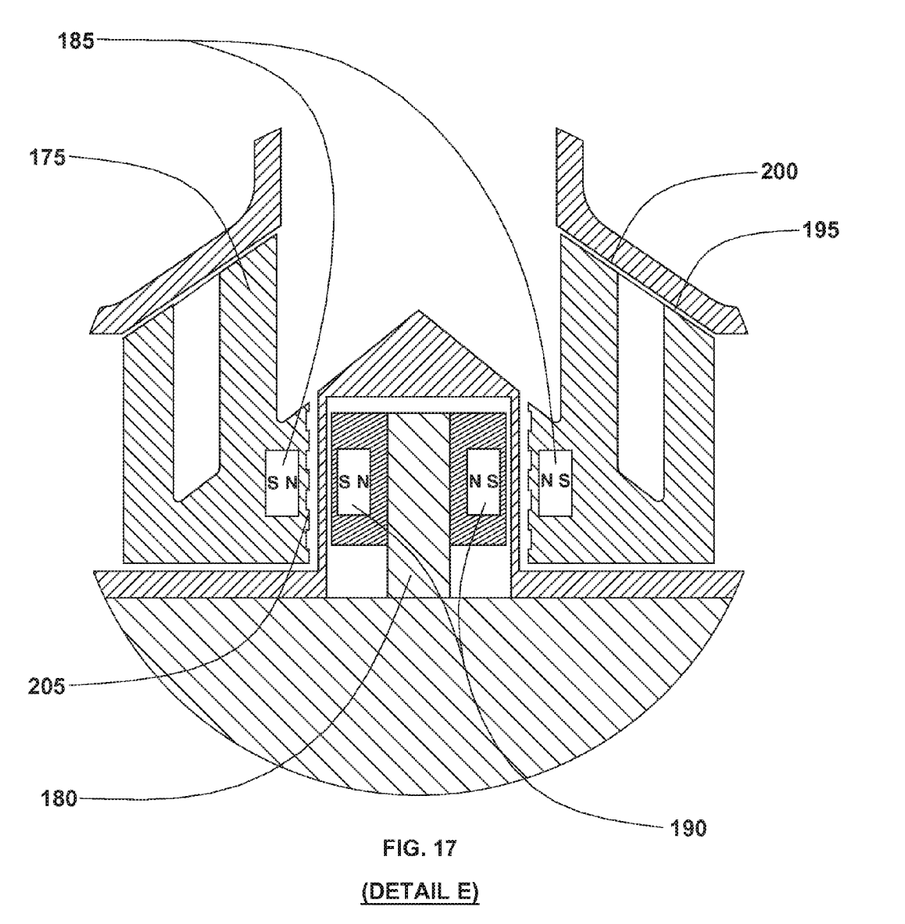
FIG. 17 is a close up cross-sectional view of an area of an embodiment of a pump with a conically shaped impeller.

FIG. 17 is a close up cross-sectional view of an area E of an illustrative embodiment of pump 170. As in the other embodiments previously discussed, internal surface 205 of impeller 175 may include pattern grooves for a hydrodynamic bearing providing radial support. Top surfaces 195 of impeller 175 are angled to provide a generally conical shaped impeller 175. FIGS. 16A-16E are views of various embodiments of impeller 175. Impeller 175 has multiple blade segments 210 that each have a top surface 195. Top surfaces 195 of blade segments 210 may be linear (FIG. 16A), convex (FIG. 16B), or concave (FIG. 16C) surfaces. Additionally, FIGS. 16D-16E are views of impeller 175 with convex and concave top surfaces 195.

One or more of the top surfaces 195 of impeller 175 may incorporate interrupted pattern grooves of any type including, but not limited to, spiral or spiral herringbone grooves. For example, the interrupted pattern grooves may be similar to the pattern grooves shown in FIGS. 12A and 12B. The arrangement of the pattern grooves on top surfaces 195 is balanced so that instability during rotation of impeller 175 is prevented or minimized. For example, all of the top surfaces 195 have pattern grooves in the embodiment shown. However, it should be recognized that in other embodiments a balanced arrangement of top surfaces 195 that have pattern grooves and do not have pattern grooves may be utilized. Flow inducing pattern grooves, such as spiral and spiral herringbone grooves, have the added benefit of producing a substantial secondary flow, particularly between top surface 195 of impeller 175 and internal surface 200 of pump housing 202. Additionally, various pattern groove types including symmetrical, asymmetrical, open, and/or dual groove patterns and various groove shapes including rectangular, rectangular with a bevel, semi-circular, and elliptical may alternatively be utilized as shown in FIGS. 9A-9K and 10A-10D. In some embodiments, top surfaces 195 of impeller 175 do not utilize pattern grooves. For example, the conical shaped impeller 175 may be a pressure balanced type impeller where the magnetic coupling formed by magnets 185 and 190 provides sole axial restraint of impeller 175.

In addition to the axial restraint provided by the magnetic coupling discussed previously, the hydrodynamic bearing provided by top surfaces 195 of impeller 175 partially restrains axial movement in the direction along the axis of rotation. Because top surfaces 195 are angled, the hydrodynamic bearing of top surfaces 195 also partially restrains radial motion of impeller 175. Thus, the hydrodynamic bearing of top surfaces 195 provides partial radial and axial support for impeller 175. The hydrodynamic bearings of top surface 195 and impeller internal surface 205 and the partial restraint provided by the magnetic coupling increase impeller stability during rotation by restraining axial and radial motion.

Figure 18:
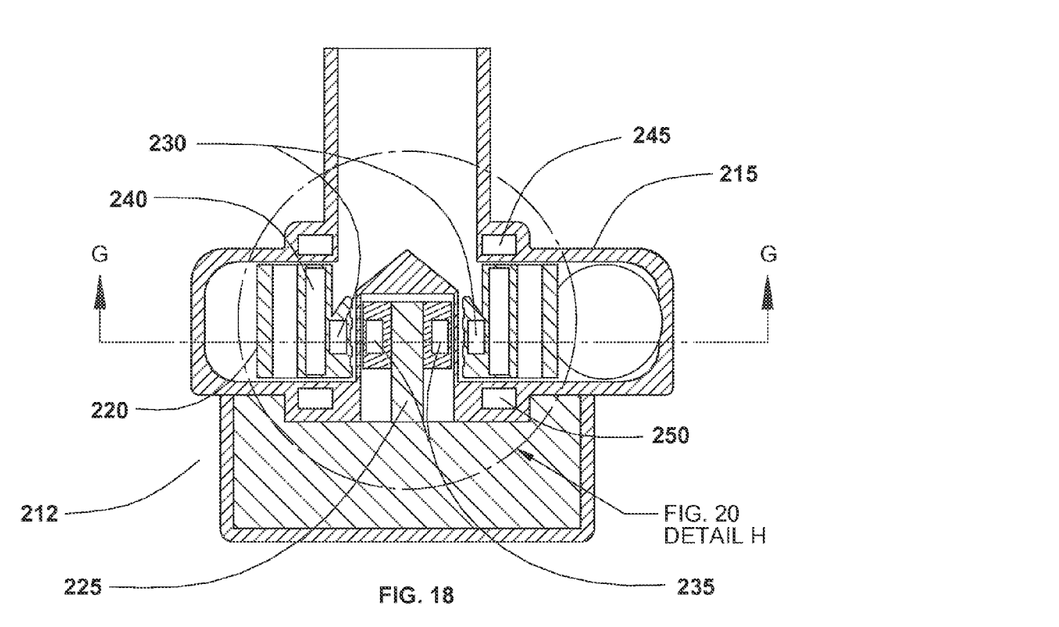
FIG. 18 is a cross-sectional side view of an illustrative embodiment of a pump with passive magnetic axial bearings.

FIG. 18 is a cross-sectional side view of an illustrative embodiment of pump housing 215 for pump 212. Many of the components of pump 212 are substantially similar to the components of the previously discussed illustrative embodiments. These similar components may operate in substantially the same manner as previously described. As in the previously discussed embodiments, impeller 220 is magnetically coupled to shaft 225. Permanent magnets 230 and 235 couple the motor to impeller 220.

Figure 20:
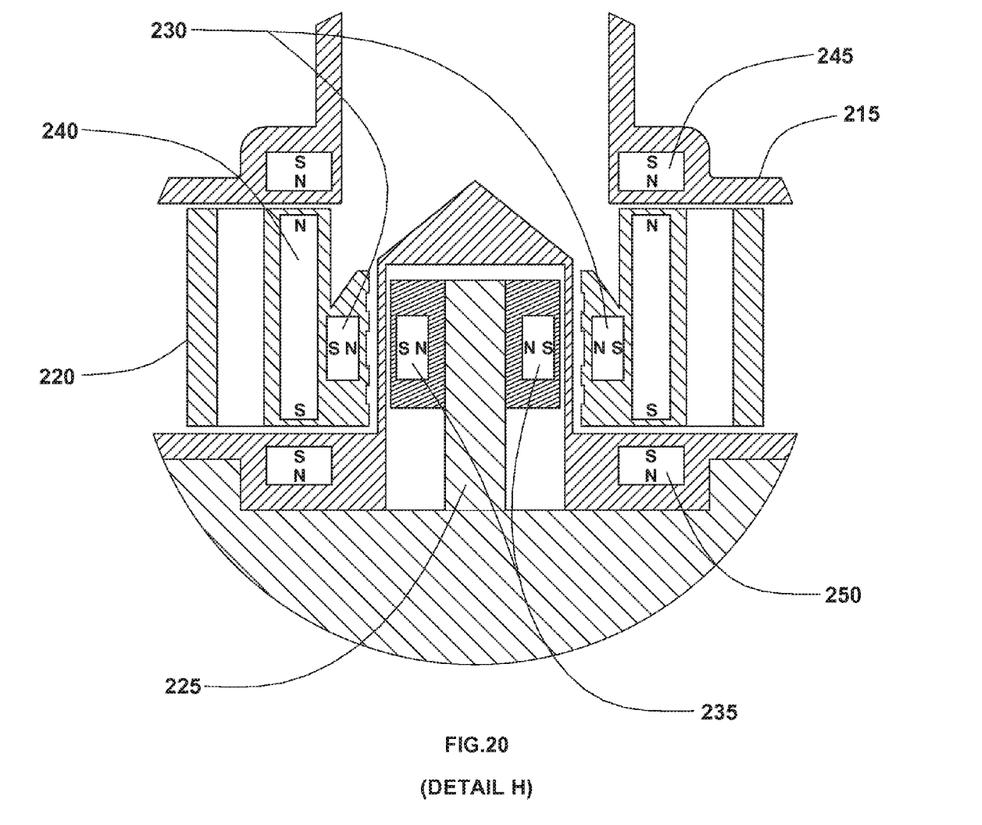
FIG. 20 is a close up cross-sectional view of an area of an illustrative embodiment of a pump with passive magnetic axial bearings.

Impeller 220 contains permanent magnets 240 and pump housing 215 contains permanent magnets 245, 250 thereby forming a magnetic thrust bearing for minimizing axial movement of impeller 220. Permanent magnets 245, 250 in housing 215 may be one or more magnets formed into a ring. FIG. 20 is a close up cross-sectional view of an area H of an illustrative embodiment of pump 212. Permanent magnets 240 in impeller 220 and permanent magnets 245 in the top portion of pump housing 215 are arranged to provide a repulsive force between impeller 220 and pump housing 215. Permanent magnets 240 in impeller 220 and permanent magnets 250 in the bottom portion of pump housing 215 are also arranged to provide a repulsive force between impeller 220 and pump housing 215. The axial restraint forces generated by magnets 240, 245, 250 are significantly greater than the attractive forces generated by the permanent magnets 230 and 235 and thereby provide sole axial support with greater stiffness for impeller 220 during rotation. Magnets 240 in impeller 220 and magnets 245, 250 in pump housing 215 provide large axial restraint forces to allow for increased clearances between impeller 220 and pump housing 215 during rotation. The increased clearances reduce damage to blood and allow for increased flow through the clearances during impeller rotation.

Figure 19:
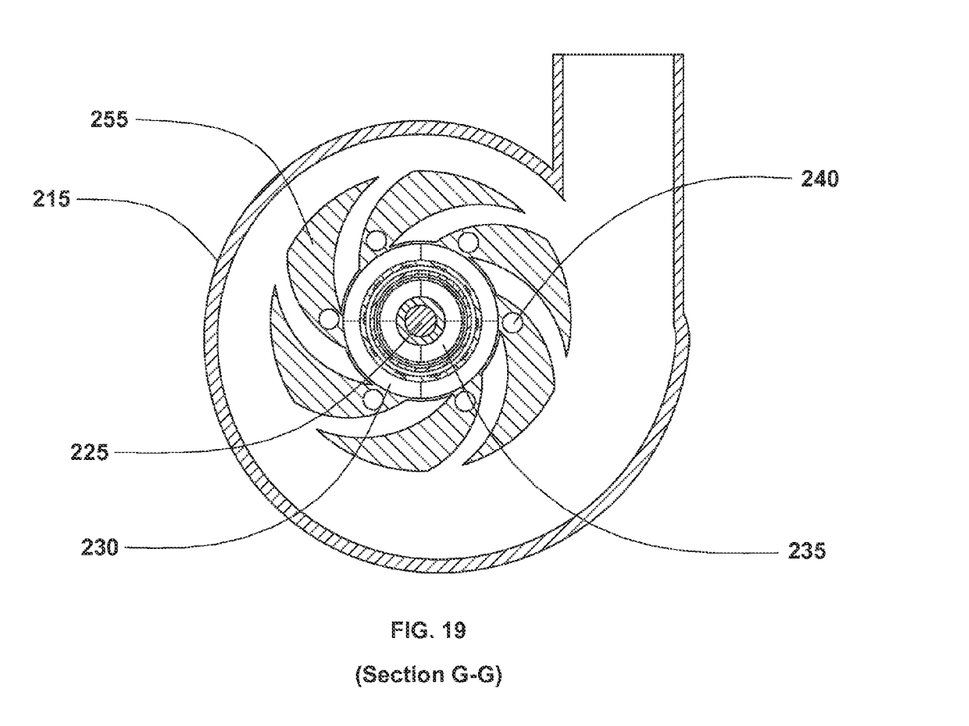
FIG. 19 is a cross-sectional top view of an illustrative embodiment of a pump with passive magnetic axial bearings.

FIG. 19 is a cross sectional top view of an illustrative embodiment of pump 212. Magnets 240 are arranged radially around impeller 220. Each blade segment 255 of impeller 220 may provide an opening/region for receiving one or more magnets 240. Additionally, in some embodiments, the top and/or bottom surfaces of impeller 220 may incorporate various pattern groove types including spiral, spiral herringbone, symmetrical, asymmetrical, open, and/or dual groove patterns. Further, various groove shapes including rectangular, rectangular with a bevel, semi-circular, and elliptical may also be utilized as shown in FIGS. 9A-9K and 10A-10D.

While the invention has been disclosed with respect to a limited number of embodiments, those skilled in the art will appreciate numerous modifications and variations can be made to those embodiments without departing from the scope of the appended claims.

The invention claimed is:

1. A blood pump comprising:
a pump housing, wherein the pump housing provides an inlet, an outlet, and a bearing surface, wherein the pump is configured to move blood from the inlet to the outlet;
an impeller housed in the pump housing and having a plurality of blades joined by a central ring having an internal surface, wherein the impeller is radially supported by a hydrodynamic bearing formed by the internal surface and the bearing surface;
a hub configured to rotate about an axis and comprising a first permanent magnet, wherein the impeller comprises a second permanent magnet located within the central ring, the first permanent magnet and the second permanent magnet (i) being arranged to attract to each other in a radial direction perpendicular to the axis, and (ii) forming a radial magnetic coupling to transmit torque from the hub to the impeller;
wherein a maximum height of the plurality of blades overlaps with each of the internal surface and the radial magnetic coupling, the maximum height being in a direction of the axis;
wherein a topmost extent of the plurality of blades is axially closer to the inlet than is (a) a topmost extent of the internal surface and (b) a bottom of the plurality of blades.

2. The blood pump of claim 1, wherein the impeller provides flow channels between circumferentially adjacent pairs of the plurality of blades.

3. The blood pump of claim 2, wherein the flow channels have a maximum height that is substantially equal to the maximum height of the plurality of blades.

4. The blood pump of claim 1, wherein each of the first permanent magnet and the second permanent magnet has a height in an axial direction parallel to the axis, and the heights of the first permanent magnet and the second permanent magnet overlap each other.

5. The blood pump of claim 1, wherein the impeller is axially supported by a magnetic thrust bearing comprising a third permanent magnet positioned in the pump housing and a fourth permanent magnet positioned in the impeller.

6. The blood pump of claim 5, wherein the fourth permanent magnet positioned in the pump housing is ring shaped.

7. The blood pump of claim 5, wherein the third permanent magnet positioned in the impeller is located within at least one of the plurality of blades.

8. The blood pump of claim 1, wherein the internal surface or the bearing surface provides at least one row of pattern grooves.

9. The blood pump of claim 1, further comprising a row of herringbone grooves on the internal surface or the bearing surface.

10. The blood pump of claim 1, wherein the internal surface or the bearing surface provides a multilobe shape.

11. The blood pump of claim 1, wherein the internal surface is substantially parallel to the bearing surface.

12. The blood pump of claim 1, wherein the internal surface is provided by an internal bore and the bearing surface is received within the bore.

13. The blood pump of claim 1, wherein top surfaces of the impeller provide a second hydrodynamic bearing for axial support of the impeller.

14. The blood pump of claim 13, wherein the top surfaces of the impeller provide at least one row of pattern grooves.

15. The blood pump of claim 13, further comprising spiral grooves or spiral herringbone grooves on the top surfaces of the impeller.

16. The blood pump of claim 1, wherein the blades are provided as an array of arc shaped segments.

17. The blood pump of claim 1, wherein the pump housing comprises a non-ferromagnetic diaphragm that houses the hub.

18. The blood pump of claim 1, wherein the impeller is an open type impeller or semi-open type impeller.

* * * * *